United States Patent
Danchin et al.

(10) Patent No.: US 10,857,135 B2
(45) Date of Patent: Dec. 8, 2020

(54) COMPOUNDS FOR TREATING DISEASES ASSOCIATED WITH A MITOCHONDRIAL DYSFUNCTION

(71) Applicant: AMABIOTICS, Paris (FR)

(72) Inventors: Antoine Danchin, Paris (FR); Agnieszka Sekowska, Paris (FR); Patrice Garnier, Venice (IT)

(73) Assignee: AMABIOTICS, Paris (FR)

( * ) Notice: Subject to any disclaimer, the term of this patent is extended or adjusted under 35 U.S.C. 154(b) by 0 days.

(21) Appl. No.: 16/328,784

(22) PCT Filed: Aug. 30, 2017

(86) PCT No.: PCT/EP2017/071812
§ 371 (c)(1),
(2) Date: Feb. 27, 2019

(87) PCT Pub. No.: WO2018/041919
PCT Pub. Date: Mar. 8, 2018

(65) Prior Publication Data
US 2019/0224174 A1   Jul. 25, 2019

(30) Foreign Application Priority Data

Aug. 30, 2016 (EP) .................................. 16306094

(51) Int. Cl.
| | |
|---|---|
| *A61K 31/437* | (2006.01) |
| *A61K 31/519* | (2006.01) |
| *A23L 33/10* | (2016.01) |
| *A61K 45/06* | (2006.01) |
| *A61K 31/7068* | (2006.01) |
| *A61P 25/16* | (2006.01) |
| *A61K 9/00* | (2006.01) |

(52) U.S. Cl.
CPC ............. *A61K 31/437* (2013.01); *A23L 33/10* (2016.08); *A61K 9/0056* (2013.01); *A61K 31/519* (2013.01); *A61K 31/7068* (2013.01); *A61K 45/06* (2013.01); *A61P 25/16* (2018.01)

(58) Field of Classification Search
CPC ............................ A61K 31/437; A61K 31/519
See application file for complete search history.

(56) References Cited

FOREIGN PATENT DOCUMENTS

| WO | WO 96/33703 | 10/1996 |
| WO | WO 2016/050804 | 4/2016 |

OTHER PUBLICATIONS

Randerath, Cancer Research, vol. 44, 1167-1171, Mar. 1984. (Year: 1984).*
Reisser, Eur J Biochem, vol. 221, 979-986, 1994. (Year: 1994).*
Johri, J PHarm Exp Therapeutics, vol. 342(3), 619-630, 2012. (Year: 2012).*
Mandemakers, J Cell Science, vol. 120, 1707-1716, 2007. (Year: 2007).*
Abou-Sleiman, P. M. et al. "Expanding insights of mitochondrial dysfunction in Parkinson's disease" *Nature Reviews Neuroscience*, Mar. 1, 2006, pp. 207-219, vol. 7, No. 3.
De Moura, M. B. et al. "Mitochondrial Dysfunction in Neurodegenerative Diseases and Cancer" *Environmental and Molecular Mutagenesis*, 2010, pp. 391-405, vol. 51, No. 5.
Modica-Napolitano, J. S. et al. "Mitochondrial dysfunction in cancer" *Mitochondrion*, Sep. 1, 2004, pp. 755-762, vol. 4, Nos. 5-6.
Ohtake, A. et al. "Diagnosis and molecular basis of mitochondrial respiratory chain, disorders: Exome sequencing for disease gene identification" *Biochimica et Biophysica Acta*, 2014, pp. 1355-1359, vol. 1840, No. 4.
Pathak, C. et al. "Modulation in the activity of lactate dehydrogenase and level of c-Myc and c-Fos by modified base queuine in cancer" *Cancer Biology & Therapy*, Jan. 1, 2008, pp. 85-91, vol. 7, Issue 1.
Vinayak, M. et al. "Queuosine modification of tRNA: its divergent role in cellular machinery" *Bioscience Reports*, 2010, pp. 135-148, vol. 30, No. 2.
Written Opinion in International Application No. PCT/EP2017/071812, dated Oct. 27, 2017, pp. 1-6.
Tatsiana Rakovich et al., "Queuosine Deficiency in Eukaryotes Compromises Tyrosine Production through Increased Tetrahydrobiopterin Oxidation", The Journal of Biological Chemistry vol. 286, No. 22, pp. 19354-19363, Jun. 3, 2011.

* cited by examiner

*Primary Examiner* — D Margaret M Seaman
(74) *Attorney, Agent, or Firm* — Alan J. Morrison (57) ABSTRACT

The present invention relates to a compound of the following formula (A):

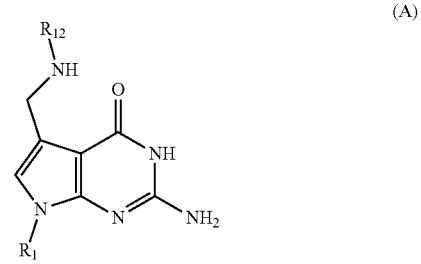

(A)

or a pharmaceutically acceptable salt or hydrate thereof, for use in the prevention or treatment of a disease associated with a mitochondrial dysfunction.

12 Claims, 2 Drawing Sheets

COMPOUNDS FOR TREATING DISEASES ASSOCIATED WITH A MITOCHONDRIAL DYSFUNCTION

CROSS-REFERENCE TO RELATED APPLICATION

This application is the U.S. national stage application of International Patent Application No. PCT/EP2017/071812, filed Aug. 30, 2017.

FIELD OF THE INVENTION

The present invention relates to compounds, pharmaceutical compositions and dietary supplements useful in the prevention or treatment of a disease associated with a mitochondrial dysfunction, in particular Parkinson's disease.

BACKGROUND OF THE INVENTION

Parkinson's disease (PD), the most common movement disorder and the second most common neurodegenerative disease after Alzheimer's disease, is characterized primarily by the loss of dopaminergic neurons in the substantia nigra pars compacta leading to a dopamine deficit in the striatum. The consequent dysregulation of basal ganglia circuitries accounts for the most prominent motor symptoms, including bradykinesia, hypokinesia, rigidity, resting tremor and postural instability. In addition to the typical motor symptoms, various non-motor features may develop, such as autonomic dysfunction, sleep disturbances, depression and cognitive impairment, indicating a more widespread degenerative process.

Little is known about the etiopathogenesis of PD. The most common sporadic form of PD seems to be a complex multifactorial disorder with variable contributions of environmental factors and genetic susceptibility, aging being the most important risk factor.

The current treatment of PD aims at correcting the consequences of the loss of dopaminergic neurones by increasing dopamine concentrations through L-DOPA administration. L-DOPA crosses the protective blood-brain barrier, whereas dopamine itself cannot, and once L-DOPA has entered the central nervous system, it is converted into dopamine by the enzyme DOPA decarboxylase. Pyridoxal phosphate (vitamin B6) is a required cofactor in this reaction, and may occasionally be administered along with L-DOPA, usually in the form of pyridoxine.

However, chronic L-DOPA administration in the treatment of Parkinson's disease induces several unwanted side-effects, such as end-of-dose deterioration of function, on/off oscillations, freezing during movement, dyskinesia at peak dose, and dopamine dysregulation syndrome as well as drug resistance (Thanvi & Lo (2004) *Postgrad. Med. J.* 80:452-458).

Accordingly, there is a need for alternative treatments to L-DOPA administration in Parkinson's disease.

SUMMARY OF THE INVENTION

Recent research on the function and dysfunction of PD-associated genes has provided fundamental new insights into biochemical pathways which are associated with the disease process. These findings have established that mitochondrial dysfunction is a common denominator of sporadic and familial PD, moving mitochondria to the forefront of PD research (Winklhofer & Haass (2010) *Biochimica et Biophysica Acta* 1802:29-44).

The present invention arises from the unexpected finding, by the present inventors, that queuine has a neuroprotective effect in an in vitro model of Parkinson's disease involving mitochondrial dysfunction.

Thus, the present invention relates to queuine, a precursor of queuine, a derivative of queuine, an analogue of queuine, or a stereoisomer of queuine, or a pharmaceutically acceptable salt or hydrate thereof, for use in the prevention or treatment of a disease associated with a mitochondrial dysfunction.

The present invention also relates to a compound of the following formula (A):

wherein:
R$_1$ represents —H or a ribosyl group of the following formula:

wherein:
R$_6$ represents —H; —O—R$_9$ or —O—CO—R$_9$ wherein R$_9$ is H, an alkyl group having from 1 to 6 carbon atoms or an aryl group having from 3 to 12 carbon atoms;

R$_7$ represents —H; —O—R$_{10}$ or —O—CO—R$_{10}$ wherein R$_{10}$ is H, an alkyl group having from 1 to 6 carbon atoms or an aryl group having from 3 to 12 carbon atoms; a deoxyribonucleic acid group; or a ribonucleic acid group;

R$_8$ represents —H; —O—R$_{11}$ or —O—CO—R$_{11}$ wherein R$_{11}$ is H, an alkyl group having from 1 to 20 carbon atoms or an aryl group having from 3 to 20 carbon atoms; a phosphate group; a diphosphate group; a triphosphate group; a deoxyribonucleic acid group; or a ribonucleic acid group;

R$_{12}$ represents a saturated or unsaturated alkyl, cycloalkyl, heterocycloalkyl or ether group having from 1 to 20 carbon atoms, optionally substituted by at least one group selected from the group consisting of:
an alkyl group having from 1 to 20 carbon atoms,
an aryl or heteroaryl group having from 3 to 20 carbon atoms,
a cycloalkyl or heterocycloalkyl group having from 3 to 20 carbon atoms, a hydroxyl group,
a carbonyl or carboxyl group having from 1 to 20 carbon atoms,
an epoxy group,
an —O—$R_4$ group wherein $R_4$ is H, an alkyl group having from 1 to 6 carbon atoms, an aryl group having from 3 to 12 carbon atoms, a glycosyl group or an aminoacyl group,
an —O—CO—$R_5$ group wherein $R_5$ is an alkyl group having from 1 to 6 carbon atoms, an aryl group having from 3 to 12 carbon atoms or a glycosyl group;
or a pharmaceutically acceptable salt or hydrate thereof,
for use in the prevention or treatment of a disease associated with a mitochondrial dysfunction in an individual.

The present invention also relates to a compound of formula (A) of the following formula (I):

(I)

wherein:
a represents a double bond or an epoxy group, and
$R_1$ represents —H or a ribosyl group of the following formula:

wherein:
$R_6$ represents —H; —O—$R_9$ or —O—CO—$R_9$ wherein $R_9$ is H, an alkyl group having from 1 to 6 carbon atoms or an aryl group having from 3 to 12 carbon atoms;
$R_7$ represents —H; —O—$R_{10}$ or —O—CO—$R_{10}$ wherein $R_{10}$ is H, an alkyl group having from 1 to 6 carbon atoms or an aryl group having from 3 to 12 carbon atoms; a deoxyribonucleic acid group; or a ribonucleic acid group;
$R_8$ represents —H; —O—$R_{11}$ or —O—CO—$R_{11}$ wherein $R_{11}$ is H, an alkyl group having from 1 to 20 carbon atoms or an aryl group having from 3 to 20 carbon atoms; a phosphate group; a diphosphate group; a triphosphate group; a deoxyribonucleic acid group; or a ribonucleic acid group;
$R_2$ and $R_3$, which are identical or different, represent —O—$R_4$ wherein $R_4$ is H, an alkyl group having from 1 to 6 carbon atoms, an aryl group having from 3 to 12 carbon atoms, a glycosyl group or an aminoacyl group;
or —O—CO—$R_5$ wherein $R_5$ is an alkyl group having from 1 to 6 carbon atoms, an aryl group having from 3 to 12 carbon atoms or a glycosyl group;
or a pharmaceutically acceptable salt or hydrate thereof,
for use in the prevention or treatment of a disease associated with a mitochondrial dysfunction.

In an embodiment of the invention, the compound of formula (A), in particular the compound of formula (I), or the pharmaceutically acceptable salt or hydrate thereof, for use as defined above, is in combination with at least one additional compound useful for the prevention or treatment of a disease associated with a mitochondrial dysfunction.

The present invention also relates to a pharmaceutical composition comprising as active substance a compound of formula (A), in particular a compound of formula (I), or a pharmaceutically acceptable salt or hydrate thereof, as defined above, optionally in association with at least one pharmaceutically acceptable excipient or vehicle, for use in the prevention or treatment of a disease associated with a mitochondrial dysfunction.

In an embodiment of the invention, the above defined pharmaceutical composition further comprises at least one additional compound useful for the prevention or treatment of a disease associated with a mitochondrial dysfunction.

The present invention also relates to a pharmaceutical composition comprising as active substance a compound of formula (A), in particular a compound of formula (I), or a pharmaceutically acceptable salt or hydrate thereof, as defined above, further comprising at least one additional compound useful for the prevention or treatment of a disease associated with a mitochondrial dysfunction, optionally in association with at least one pharmaceutically acceptable excipient or vehicle.

The present invention also relates to products comprising:
a compound of formula (A), in particular a compound of formula (I), or a pharmaceutically acceptable salt or hydrate thereof, as defined above,
at least one additional compound useful for the prevention or treatment of a disease associated with a mitochondrial dysfunction,
as a combined preparation for simultaneous, separated or sequential use in the prevention or treatment of a disease associated with a mitochondrial dysfunction in an individual.

The present invention also relates to a dietary supplement comprising a compound of formula (A), in particular a compound of formula (I), or a pharmaceutically acceptable salt or hydrate thereof, as defined above, for use for reducing the risk of a disease associated with a mitochondrial dysfunction.

In an embodiment of the invention, the dietary supplement as defined above, optionally comprises additional compounds, preferably selected from the group consisting of vitamins, minerals, fatty acids, amino acids and antioxidants.

The present invention also relates to a method for the prevention or treatment of a disease associated with a mitochondrial dysfunction in an individual, comprising administering to the individual an effective amount of a compound of formula (A), in particular a compound of formula (I), or of a pharmaceutically acceptable salt or hydrate thereof, as defined above.

In an embodiment of the invention, the method as defined above further comprises the administration of at least one compound useful for the prevention or treatment of a disease associated with a mitochondrial dysfunction.

The present invention also relates to the use of a compound of formula (A), in particular a compound of formula (I), as defined above for the manufacture of a medicament intended for the prevention or treatment of a disease associated with a mitochondrial dysfunction in an individual.

In an embodiment of the invention, the medicament as defined above further comprises at least one compound useful for the prevention or treatment of a disease associated with a mitochondrial dysfunction.

DETAILED DESCRIPTION OF THE INVENTION

Compound of Formula (A)

Compounds of formula (A), in particular compounds of formula (I), as defined above can be readily chemically synthesized by one of skill in the art, as is in particular described in Barnett & Grubb (2000), Tetrahedron 56: 9221-9225, Oxenford et al. (2004) Tetrahedron Letters 45:9053-9055, Brooks et al. (2010) Tetrahedron Letters 51: 4163-4165, Gerber et al. (2012) Org. Biomol. Chem. 10: 8660-8668, the thesis by Allen Brook entitled "Synthesis of Tritium Labeled Queuine, PreQ$_1$ and Related Azide Probes Toward Examining the Prevalence of Queuine" (2012, University of Michigan), Akimoto et al. (1986) J. Med. Chem., 29: 1749-1753, Kelly et al. (2016) Nucleic Acids Research, 1-11, and international application WO2016/050806, all of which are incorporated herein by reference.

Briefly, by way of example, queuine can be synthesised according to the following reaction scheme:

In additions, compounds of formula (A), in particular compounds of formula (I), as defined above may be extracted and optionally purified from natural sources such as microorganisms, in particular bacteria, or from plants, in particular from plants nodulated with alpha-Proteobacteria such as bacteria of the *Rhizobium, Mesorhizobium*, and *Sinorhizobium* genii.

By way of example, queuosine can be obtained from tRNAs, in particular tRNA$^{Asn}$, tRNA$^{Asp}$, tRNA$^{His}$ and tRNA$^{Tyr}$, prepared as follows:

Preparation of Total RNA Under Acidic Conditions
B. subtilis strains (or other relevant bacteria) are grown in ED liquid medium with appropriate supplements at 37° C. with constant aeration. Fresh overnight cultures are inoculated in 15 ml of ED medium to an optical density at 600 nm (OD600) of 0.1. Cells are grown at 37° C. to OD600 of 1 and chilled in equal volume of 60% methanol in 70 mM Hepes pH 7.5 at −80° C. All subsequent steps are carried out in the cold and the solution for prepared crude RNA are treated with diethyl pyrocarbonate and sterilized. Cells are pelleted at 4° C., washed in water and resuspended in 0.5 ml of 10% glucose, 11 mM Tris, 10 mM EDTA. The suspensions are transferred to tubes containing 0.1 g glass beads acid-washed (sigma-Aldrich, G4649). Tubes are disposed into The CoolPrep Adapter of FastPrep®-24 Instrument (MP Biomedicals) containing 50 g of dry ice. Cells are broken after three cycles using following parameters: 6 meters per second during 45 s. After each cycle, suspensions are kept 1 min on ice. After centrifugation 2 min at 10,000 rpm, the supernatants are transferred to a fresh eppendorf tube. 0.3 M sodium acetate pH 5.2 is added and total RNA is isolated under acidic conditions. One volume of acid phenol:chloroform with Isoamyl alcohol (125:24:1) pH 4.5 (Amresco, AM9720) is added. The sample are mixed by vortexing 10 s and incubated for 3 min in a 65° C. water-bath. The phases are separated by spinning 5 min at 14,000 rpm, then the aqueous phase is re-extracted once with the same hot acid phenol procedure. The aqueous phase is transferred to a new tube and supplemented by one volume of cold acid phenol. After centrifugation 5 min at 14,000 rpm, RNA are precipitated with 2.5 volumes of absolute ethanol 1 h at −80° C. The RNA is pelleted at 14,000 rpm for 15 min at 4° C. and washed with 70% ethanol. The RNA pellet is dissolved in 10 mM Tris, 1 mM EDTA pH 7.5.

Enrichment of tRNA
The total RNA preparation is then mixed with one volume of lithium chloride 8 M pH 4.5 and sodium acetate pH 5.2 at 0.01 mM final concentration. This RNA solution is incubated 2 h at −80° C. After centrifugation at 14,000 rpm for 15 min at 4° C., the tRNA remained in supernatant. To remove salt contamination, tRNA is precipitated 1 h at −80° C. by addition of 0.3 M sodium acetate pH 5.2 and 2.5 volumes of absolute ethanol. Then, tRNA is pelleted by centrifugation at 14,000 rpm for 15 min at 4° C. and washed with 70% ethanol. The tRNA pellet is dissolved in 10 mM Tris, 1 mM EDTA pH 7.5.

The stereoisomer of queuine according to the invention can be of any type. Preferably, the stereoisomer of queuine is ent-queuine.

The pharmaceutical acceptable salt or hydrate according to the invention can be of any type. However, it is preferred that the pharmaceutical acceptable salt according to the invention is a hydrochloride salt.

Preferably, the glycosyl group according to the invention is selected from the group consisting of a mannosyl group, a galactosyl group or a glutamyl group.

Preferably, the aminoacyl group is selected from alanine (ala, A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y) and valine (val, V).

Preferably, the substituents of formula (A), in particular of formula (I), according to the invention may be linked together.

In a preferred embodiment of the compound of formula (A) as defined above:
$R_1$ is H, and
$R_{12}$ represents a saturated or unsaturated alkyl, cycloalkyl, heterocycloalkyl or ether group having from 1 to 20 carbon atoms, optionally substituted by at least one group selected from the group consisting of:
an alkyl group having from 1 to 20 carbon atoms,
an aryl or heteroaryl group having from 3 to 20 carbon atoms,
a cycloalkyl or heterocycloalkyl group having from 3 to 20 carbon atoms,
a hydroxyl group,
a carbonyl or carboxyl group having from 1 to 20 carbon atoms,
an epoxy group,
an —O—$R_4$ group wherein $R_4$ is H, an alkyl group having from 1 to 6 carbon atoms, an aryl group having from 3 to 12 carbon atoms, a glycosyl group or an aminoacyl group,
an —O—CO—$R_5$ group wherein $R_5$ is an alkyl group having from 1 to 6 carbon atoms, an aryl group having from 3 to 12 carbon atoms or a glycosyl group.

In another preferred embodiment of the compound of formula (A) as defined above:
$R_{12}$ represent a group of the following formula:

wherein:
a represents a double bond or an epoxy group, and
$R_2$ and $R_3$, which are identical or different, represent —O—$R_4$ wherein $R_4$ is H, an alkyl group having from 1 to 6 carbon atoms, an aryl group having from 3 to 12 carbon atoms, a glycosyl group or an aminoacyl group; or —O—CO—$R_5$ wherein $R_5$ is an alkyl group having from 1 to 6 carbon atoms, an aryl group having from 3 to 12 carbon atoms or a glycosyl group.

In another preferred embodiment of the compound of formula (A), as defined above:
$R_1$ is H, and
$R_{12}$ represents a saturated or unsaturated alkyl group having from 1 to 20 carbon atoms, optionally substituted by at least one of a hydroxyl group.

In another preferred embodiment of the compound of formula (A), in particular of the compound of formula (I), as defined above:
$R_2$ and $R_3$, which are identical or different, represent —OH, a —O-mannosyl group, a —O-galactosyl group or a —O-glutamyl group;
$R_6$ represents —OH;
$R_7$ and $R_8$, which are identical or different, represent —OH or a ribonucleic acid group.

Preferably, when $R_7$ and $R_8$ both represent a ribonucleic acid group, the compound of formula (A), in particular the compound of formula (I), according to the invention is included in a transfer RNA (tRNA) as a ribonucleoside of the tRNA. More preferably, the compound of formula (A), in particular the compound of formula (I), according to the invention is a ribonucleoside of the anticodon of the tRNA, most preferably the first nucleoside of the anticodon, i.e. the 5' nucleoside of the anticodon or the nucleoside in the wobble position of the anticodon. Preferred tRNAs according to the invention are selected from the list consisting of tRNA$^{Asn}$, tRNA$^{Asp}$, tRNA$^{His}$ and tRNA$^{Tyr}$.

Preferably, the compound of formula (A), in particular the compound of formula (I), as defined above is represented by the following formulae (II), (III) or (IV):

-continued

(III)

(IV)

Preferably, when a compound of formula (A), in particular a compound of formulae (I)-(III), according to the invention is included in a tRNA$^{Asp}$, then $R_3$ is OH and $R_2$ is O-mannose.

Preferably also, when a compound of formula (A), in particular a compound of formulae (I)-(III), according to the invention is included in a tRNA$^{Tyr}$, then $R_3$ is OH and $R_2$ is O-galactose.

Preferably, the compound of formula (A), in particular the compound of formula (I), according to the invention is represented by the following formula (V):

(V)

As should be clear to one of skill in the art, all the stereochemical configurations of the compounds according to the invention are intended to be covered by the formulae shown herein. In particular, as is intended herein, when the stereoconfiguration of a bond is not specified, the bond may represent any of an upward bond, a downward bond, and a mixture of the two, in particular a 1/1 mixture of the two.

Thus, the compound of formula (A), in particular the compound of formula (I), according to the invention also relates to the optically active forms of the compound of formula (V), such as the enantiomers represented by the following formulae (Va) and (Vb):

(Va)

(Vb)

or their mixtures, in particular a racemic mixture thereof.

The compound of formula (Va) is queuine. Queuine, is also known as 7-(3,4-trans-4,5-cis-dihydroxy-1-cyclopenten-3-ylaminomethyl)-7-deazaguanine.

The compound of formula (Vb) is ent-queuine.

Preferably, the compound of formula (A), in particular the compound of formula (I), according to the invention is represented by the following formulae (VI), (VIa), (VIb), (VII), (VIIa), (VIIb), (VIII), (VIIIa), (VIIIb), (IX), (X), (Xa) or (Xb):

(VI)

(VIa)

(VIb)

(VII)

(VIIa)

(VIIb)

(VIII)

(VIIIa)

(VIIIb)

(IX)

(X)

(Xa)

(Xb)

Preferably also, the compound of formula (A) according to the invention is represented by the following formulae (XI), (XIa), (XIb), (XII), (XIII), (XIV), (XV), (XVI) or (XVII):

(XI)

(XIa)

(XIb)

(XII)

(XIII)

(XIV)

(XV)

(XVI)

(XVII)

The compound of formula (VIa) is epoxyqueuine, also known as 7-(5-[3,4-epoxy-2,5-dihydroxycyclopent-1-yl)amino]methyl)-7-deazaguanine.

The compound of formula (VIIa) is queuosine also known as 2-amino-5-({[(1S,4S,5R)-4,5-dihydroxycyclopent-2-en-1-yl]amino}methyl)-7-(β-D-ribofuranosyl)-1,7-dihydro-4H-pyrrolo [2,3-d]pyrimidin-4-one.

The compound of formula (VIIIa) is epoxyqueuosine also known as 5 7-(5-[(3,4-epoxy-2,5-dihydroxycyclopent-1-yl)amino]methyl)-7-deazaguanosine.

The compound of formula (XI) is N-((2-amino-4-oxo-4,7-dihydro-3H-pyrrolo[2,3-d]pyrimidin-5-yl)methyl)-2,3-dihydroxypropan-1-amine.

The compound of formula (XII) is N-((2-amino-4-oxo-4,7-dihydro-3Hpyrrolo[2,3-d]pyrimidin-5-yl)methyl)-3-phenylpropan-1-amine.

The compound of formula (XIII) is N-((2-amino-4-oxo-4,7-dihydro-3H pyrrolo[2,3-d]pyrimidin-5-yl)methyl)-propan-1-amine.

The compound of formula (XVI) is N-((2-amino-4-oxo-4,7-dihydro-3Hpyrrolo[2,3-d]pyrimidin-5-yl)methyl)-butan-1-amine.

The compound (XVII) is N-((2-amino-4-oxo-4,7-dihydro-3Hpyrrolo[2,3-d]pyrimidin-5-yl)methyl)-hexan-1-amine.

Preferably, the compound of formula (A), in particular the compound of formula (I), according to the invention is selected from the group consisting of mannosyl-queuine, galactosyl-queuine, glutamyl-queuine, galactosyl-queuosine, mannosyl-queuosine, glutamyl-queuosine, queuine-tRNA, and epoxyqueuine-tRNA.

Preferably also the compound of formula (A), in particular the compound of formula (I), according to the invention is selected from the group consisting of queuine-tRNA[Asp], queuine-tRNA[Tyr], epoxyqueuine-tRNA[Asp], epoxyqueuine-tRNA[Tyr], queuine-tRNA[Asn], queuine-tRNA[His], epoxyqueuine-tRNA[Asn], epoxyqueuine-tRNA[His], mannosyl-queuine-tRNA[Asp], galactosyl-queuine-tRNA[Tyr], mannosyl-epoxyqueuine-tRNA[Asp], and galactosyl-epoxyqueuine-tRNA[Tyr].

Most preferably also the compound of formula (A), in particular the compound of formula (I), according to the invention is selected form the group consisting of queuine, ent-queuine, queuosine, epoxyqueuine, epoxyqueuosine, mannosyl-queuine, galactosyl-queuine, glutamyl-queuine, galactosyl-queuosine, mannosyl-queuosine, glutamyl-queuosine, queuine-tRNA, epoxyqueuine-tRNA, a compound of formula (XI), (XIa) and (XIb).

Disease Associated with a Mitochondrial Dysfunction

As intended herein the expression "disease associated with a mitochondrial dysfunction" encompasses diseases linked to or caused by a mitochondrial dysfunction, disorder, or disease.

Preferably, the disease associated with a mitochondrial dysfunction according to the invention is a neuronal disease associated with a mitochondrial dysfunction, more preferably a central nervous system disease associated with a mitochondrial dysfunction and most preferably a neurodegenerative disease associated with a mitochondrial dysfunction.

Preferably, the disease associated with a mitochondrial dysfunction according to the invention is Parkinson's disease.

Parkinson's disease is well known to one of skill in the art and is notably defined in sections G20, G21 and G22 of ICD-10 Version: 2016.

As intended herein Parkinson's disease according to the invention notably encompasses:
  primary (idiopathic) parkinsonism,
  secondary parkinsonism (acquired),
  atypical parkinsonism, and
  familial neurodegenerative disease causing parkinsonism.

Parkinson's disease according to the invention also encompasses sporadic and familial Parkinson's disease.

Parkinson's disease according to the invention notably also encompasses stage I, stage II, stage III, stage IV and stage V Parkinson's disease.

Individual

As intended herein the individual according to the invention is preferably a human.

Preferably, the individual according to the invention is more than 30, 40, 50, 60, 70 or 80 years old.

Preferably also, the individual according to the invention is less than 80, 70, 60, 50, or 40 years old.

Preferably also, the individual according to the invention is an individual with a stage I, II, III, IV or V Parkinson's disease.

Preferably also, the individual according to the invention is not afflicted with Parkinson's disease or presents with no Parkinson's disease symptoms and is at risk of developing Parkinson's disease. More preferably, the individual according to the invention is not afflicted with Parkinson's disease or presents with no Parkinson's disease symptoms and at least one of the individual's relative suffers from Parkinson's disease.

Additional Compound

The additional compound useful for the prevention or treatment of a disease associated with a mitochondrial dysfunction can be of any type known to one of skill in the art. Preferably, the additional compound according to the invention is selected from the group consisting of vitamins, minerals, fatty acids, amino acids, antioxidants and derivatives or precursors thereof.

Preferably vitamins are selected from the group consisting of pyridoxine, pyridoxal phosphate (Vitamin $B_6$), riboflavin, thiamine, vitamin E, vitamin K3, vitamin C, niacin, CoQ10 and β-carotene.

Preferably, minerals are selected from the group consisting of calcium, magnesium, selenium and phosphorus.

Preferably, the amino-acid is L-DOPA (levodopa).

Preferably, the fatty acids are selected from the group consisting of Levo-carnitine and acetyl-L-carnitine.

Administration

As intended herein, "combined" or "in combination" means that the compound of formula (A), in particular the compound of formula (I), as defined above, is administered at the same time than another compound or product, either together, i.e. at the same administration site, or separately, or at different times, provided that the time period during which the compound of formula (A), in particular the compound of formula (I), as defined above exerts its effects on the individual and the time period during which the additional agent or product exerts its pharmacological effects on the individual, at least partially intersect.

Preferably, the compound of formula (A), in particular the compound of formula (I), according to the invention or the pharmaceutically acceptable salt or hydrate thereof is for an administration or is administered at a dosage regimen of from 0.01 to 40 mg/kg/d, more preferably of from 0.01 to 10 mg/kg, even more preferably of from 0.01 to 1 mg/kg/d, and most preferably of from 0.01 to 0.1 mg/kg/d.

Preferably, the compound of formula (A), in particular the compound of formula (I), according to the invention or the pharmaceutically acceptable salt or hydrate thereof is in a form suitable for an administration or is administered by the oral route, the intradermal route, the intravenous route, the intramuscular route or the subcutaneous route. Preferably, the compound of formula (A), in particular the compound of formula (I), according to the invention, or the pharmaceutical composition, medicament, products or dietary supplement comprising it is in a form suitable for an administration or is administered by a hypodermic implant.

Preferably, the compound of formula (A), in particular the compound of formula (I), according to the invention, or the pharmaceutical composition, medicament, products or dietary supplement comprising it is the form of a powder, sachets, tablets, gelatine, capsules, or a liquid or gel solution.

Preferably also, the pharmaceutical composition, medicament, products or dietary supplement according to the invention, comprises the compound of formula (A), notably the compound of formula (I), according to the invention, in particular queuine, ent-queuine, queuosine, or a compound of formula (XI), (XIa) or (XIb), at a unit dose of at least 0.15 mg, 1 mg, 10 mg, 50 mg, 100 mg, 500 mg or 1000 mg.

Preferably also, the pharmaceutical composition, medicament, products or dietary supplement according to the invention, comprises an extract, in particular a purified extract, from microorganism and/or plant, which comprises the compound of formula (A), notably the compound of formula (I), according to the invention, in particular queuine, ent-queuine, queuosine, or a compound of formula (XI), (XIa), or (XIb), in particular at a unit dose of at least 0.15 mg, 1 mg, 10 mg, 50 mg, 100 mg, 500 mg or 1000 mg.

EXAMPLE 6-hydroxydopamine (6-OHDA) is a selective catecholaminergic neurotoxin that is not only used as a pharmacological agent able to trigger Parkinson's disease-like stigmata (Sauer and Ortel (1994) *Neuroscience* 59:401-15; Cass et al. (2002) *Brain Res.* 938:29-37) but also likely corresponds to a natural dopaminergic catabolite that accumulates in Parkinson's disease-affected brains and that appears to strongly contribute to this pathology (Ellenberg et al. (1995) in "*Etiology of Parkinson's Disease*", eds Ellenberg, Koller, Langston (Marcel Dekker, New York), pp 153-201; Jellinger et al. (1995) *J. Neural. Transm.* 46:297-314).

For this reason, 6-OHDA-induced dopaminergic neurotoxicity in rats is widely used as a model for PD research (Simola et al. (2007) *Neurotox. Res.* 11:151-167; Mercanti (2012) *Methods Mol. Biol.* 846:355-364; De Jesus-Cortes et al. (2015) *npj Parkinson's Disease* 1:15010). Besides, 6-OHDA has been shown to impair mitochondrial function in this rat model of Parkinson's disease, which would allow the detection of distinct mitochondrial dysfunction as a suitable surrogate marker for the preclinical assessment of potential neuroprotective strategies (Kupsch et al. (2014) *J. Neural. Transm.* 121:1245-1257).

In this regard, 6-OHDA-induced neurodegeneration of dopaminergic neurones in vitro, also provides a useful model of Parkinson's disease, especially as regards the restoration of mitochondria function (Wei et al. (2015) *Translational Neurodegeneration* 4:11).

Accordingly, this study investigates the effect of queuine on rat primary mesencephalic cultures injured by exposure to 6-OHDA. The brain-derived neurotrophic factor (BDNF) has been suggested to reduce 6-OHDA-induced neurodegeneration in vitro and is used as positive control.

1. Material and methods
1.1. Compounds

6-OHDA is obtained from Sigma (ref: H116).

Queuine is synthesized according to Brooks et al. (2010) *Tetrahedron Letters* 51:4163-4165 and the thesis by Allen Brooks entitled "*Synthesis of Tritium Labeled Queuine, PreQ1 and Related Azide Probes Toward Examining the Prevalence of Queuine*" (2012, University of Michigan).

BDNF is obtained from PanBiotech (Ref: CB-1115002).

In the following experiments 6-OHDA, Queuine and BDNF are suspended in the culture medium defined below.

1.2. Rat Primary Cultures of Dopaminergic Neurons

Rat dopaminergic neurons are cultured as described by Schinelli et al. (1988) *J. Neurochem.* 50:1900-1907.

Briefly, pregnant female rats (Wistar rats; Janvier) at 15 days of gestation are killed by cervical dislocation and the fetuses are removed from the uterus. The embryonic midbrains are removed and placed in ice-cold Leibovitz medium (L15; PanBiotech) containing 2% of Penicillin-Streptomycin (PS; PanBiotech) and 1% of bovine serum albumin (BSA; PanBiotech). Only the ventral portions of the mesencephalic flexure is used for cell preparations as this is the region of the developing brain rich in dopaminergic neurons. The midbrain is dissociated by trypsinisation for 20 min at 37° C. (Trypsin EDTA 1×; PanBiotech). The reaction is stopped by the addition of Dulbecco's modified Eagle's medium (DMEM; PanBiotech) containing DNAse I grade II (0.1 mg/mL; Roche Diagnostic) and 10% of fetal calf serum (FCS; Invitrogen). The cells are mechanically dissociated by 3 passages through a 10 ml pipette. The dissociated cells are then centrifuged at 180×g for 10 min at 4° C. on a layer of BSA (3.5%) in L15 medium. The supernatant is discarded and the pelleted cells are re-suspended in a culture medium consisting of Neurobasal (Invitrogen, Ref: 21103, Batch: 1725098) supplemented with B27 (2%; Invitrogen, ref: 17504), L-glutamine (2 mM; PanBiotech, Ref: P04-80100) and 2% of PS, 10 ng/mL of BDNF (PanBiotech, Ref: CB-1115002) and 1 ng/mL of GDNF (PanBiotech, Ref: CB-1116001). Viable cells are counted in a Neubauer cytometer using the trypan blue exclusion test. The cells are then seeded at a density of 40 000 cells/well in 96 well-plates pre-coated with poly-D-lysine (Greiner) and are cultured at 37° C. in a humidified air (95%)/CO2 (5%) atmosphere. Half of the medium is changed every 2 days with fresh medium. In these conditions, after 5 days of culture, astrocytes are present in the culture and release growth factor allowing neurons differentiation. Five to six percent of the neuronal cell population are dopaminergic neurons.

1.3. Assessment of Neuroprotective Effect on Rat Dopaminergic Neurons

The neuroprotective effect of queuine is assessed on 6-days old cultures according to the following protocol:
  Addition of control medium (Culture medium);
  Addition of 6-OHDA (20 µM, 48H)+Culture medium;
  Addition of 6-OHDA (20 µM, 48H)+BDNF (50 ng/ml);
  Addition of 6-OHDA (20 µM, 48H)+queuine (7 concentrations from 0.03 µM to 30 µM) added at three different times before, during or after 6-OHDA intoxication:
    6 days before 6-OHDA intoxication, the compound will stay in the medium until intoxication;
    1 day before 6-OHDA intoxication
    1 day after intoxication
  The same conditions without 6-OHDA (no intoxication) are tested in parallel to assess the effects of queuine on dopaminergic neurons survival.
Each condition is replicated in six wells of the 96-wells culture plates.

1.4. End Point Evaluation: Determination of the Total Number of Dopaminergic Neurons At the end of the incubation time, the cells are fixed by a solution of 4% paraformaldehyde for 20 min at room temperature. The cells are then permeabilized and nonspecific sites are blocked with a solution of phosphate buffered saline (PBS; PanBiotech) containing 0.1% of saponin (Sigma) and 1% fetal calf serum (FCS) for 15 min at room temperature. Eventually, the cells are incubated with a monoclonal anti-Tyrosine Hydroxylase (TH) mouse antibody (Sigma) in PBS containing 1% FCS and 0.1% saponin, for 2 h at room temperature. The anti-TH antibody targets dopaminergic neurons.

The antibody is revealed with an Alexa Fluor 488-labelled goat anti-mouse IgG (Molecular probe) in PBS with 1% FCS, 0.1% saponin, for 1 h at room temperature. The nuclei of the cells is stained by a fluorescent marker (Hoechst solution, SIGMA) in the same solution.

For each condition, 20 pictures per well are taken using InCell Analyzer™ 2000 (GE Healthcare) with 20× magnification. Images of each culture well are also taken.

The analysis of the cell bodies of TH positive neurons are performed using Developer software (GE healthcare). A total of 6 data per experimental condition is provided. All values are expressed as mean±s.e. mean. For statistical analyses ANOVA is performed followed by Dunnett's test.

2. Results

Preliminary results indicate that queuine has a neuroprotective effect on 6-OHDA-induced neurotoxicity.

Figure 1:
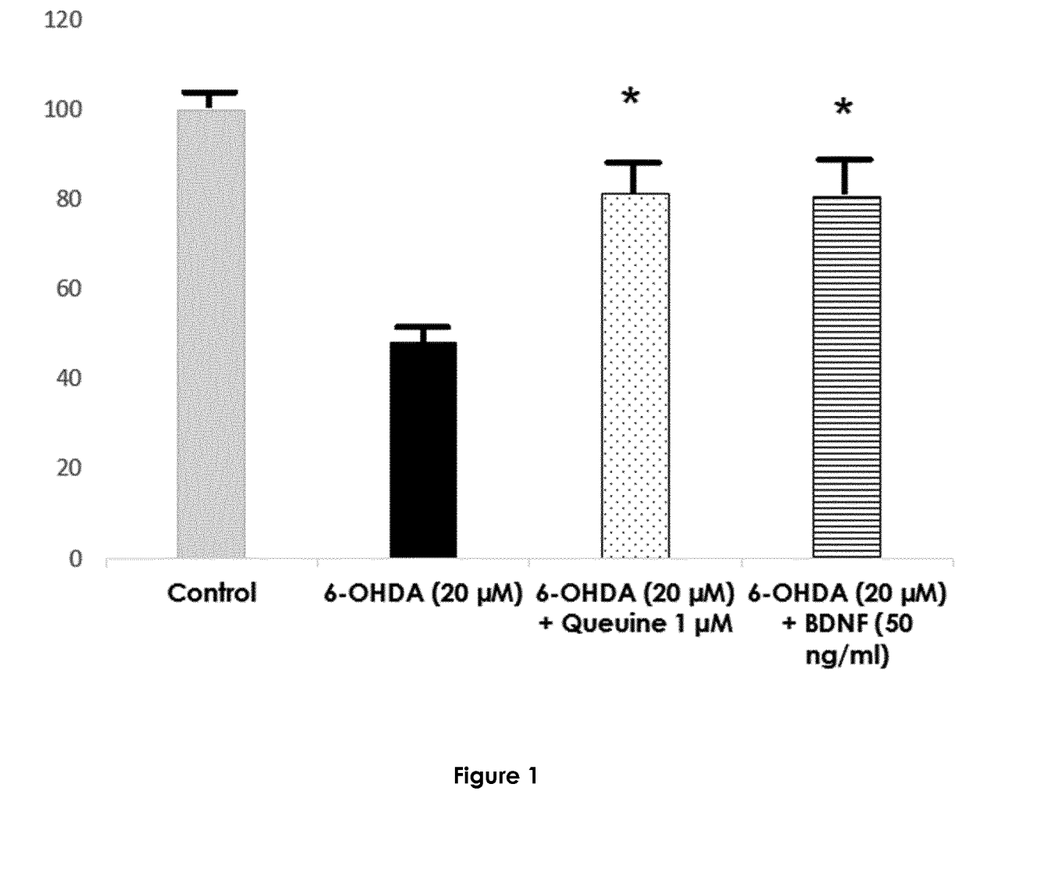
FIG. 1 represents the survival of primary dopaminergic neuron culture expressed in % of control in absence of 6-OHDA (gray bar, control), with 6-OHDA alone (black bar), with 6-OHDA+queuine added 1 day before 6-OHDA intoxication (dotted bar), and with 6-OHDA+BDNF. * represents p<0.05 vs 6-OHDA.
Figure 2:
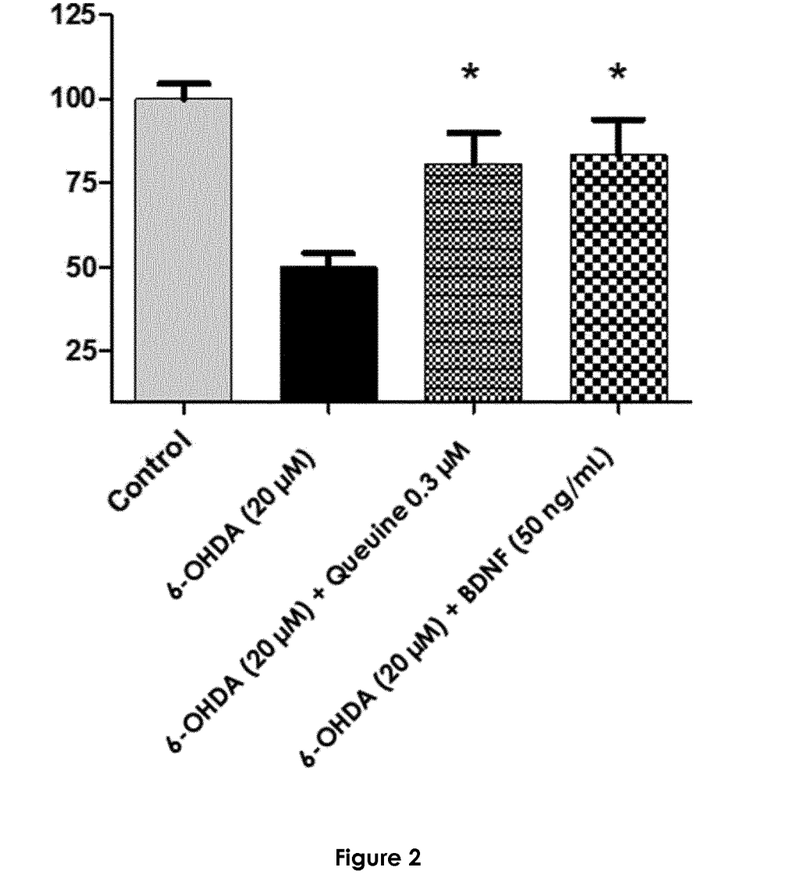
FIG. 2 represents the survival of primary dopaminergic neuron culture expressed in % of control in absence of 6-OHDA (gray bar, control), with 6-OHDA alone (black bar), with 6-OHDA+queuine added 6 days before 6-OHDA intoxication (small dot bar), and with 6-OHDA+BDNF (large dot bar). * represents p<0.05 vs 6-OHDA.

As such, according to FIG. 1 and FIG. 2, 6-OHDA applied at 20 µM for 48 h induces a large and significant decrease of TH positive neurons. Application of BDNF (50 ng/mL) 1 day and 6 days before 6-OHDA intoxication displays a protective effect against 6-OHDA injury (*, $p<0.05$, 80.80% of the control in FIG. 1, and *, $p<0.05$, 83.44% of the control in FIG. 2). These results validate the study.

Moreover, FIG. 1 shows that queuine at 1 µM presents a significant protective effect against 6-OHDA (*, $p<0.05$, 81.33% of the control) when added 1 day (24 hours) before 6-OHDA intoxication. In addition, FIG. 2 shows that queuine at 0.3 µM has a significant protective effect against 6-OHDA intoxication (*, $p<0.05$, 80.47% of the control) when added 6 days before 6-OHDA intoxication.

The invention claimed is:

1. A product comprising queuine and L-DOPA as a combined preparation.

2. A method for causing a protective effect on dopamanergic neurons in an individual having Parkinson's disease comprising administering queuine to the individual.

3. The method of claim 2, wherein queuine is administered in a dosage regimen of 0.01 to 40 mg/kg/d.

4. The method of claim 3, wherein queuine is administered in a dosage regimen of 0.01 to 10 mg/kg/d.

5. The method of claim 4, wherein queuine is administered in a dosage regimen of 0.01 to 1 mg/kg/d.

6. The method of claim 5, wherein queuine is administered in a dosage regimen of 0.01 to 0.1 mg/kg/d.

7. The method of claim 2, wherein queuine is administered orally, intradermally, intravenously, intramuscularly, or subcutaneously.

8. The method of claim 2, wherein queuine is administered in combination with L-DOPA.

9. The method of claim 2, wherein queuine is administered in the form of a pharmaceutical composition comprising at least one pharmaceutically acceptable excipient or vehicle and queuine.

10. The method of claim 9, wherein the pharmaceutical composition comprises L-DOPA.

11. The method of claim 2, wherein queuine is formulated as a dietary supplement.

12. The method of claim 11, wherein the dietary supplement comprises additional compounds selected from the group consisting of vitamins, minerals, fatty acids, amino acids, and antioxidants.

* * * * *